US008775095B2

(12) United States Patent
Walling et al.

(10) Patent No.: US 8,775,095 B2
(45) Date of Patent: Jul. 8, 2014

(54) METHODS AND APPARATUS FOR DECENTRALIZED DIABETES MONITORING

(75) Inventors: Paul Douglas Walling, Indianapolis, IN (US); Nigel Surridge, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1015 days.

(21) Appl. No.: 12/818,781

(22) Filed: Jun. 18, 2010

(65) Prior Publication Data
US 2011/0313673 A1 Dec. 22, 2011

(51) Int. Cl.
G01N 33/50 (2006.01)
G06F 19/00 (2011.01)

(52) U.S. Cl.
USPC .................................. 702/19; 73/61

(58) Field of Classification Search
USPC ........................................... 702/19
See application file for complete search history.

(56) References Cited

U.S. PATENT DOCUMENTS

| | | | | |
|---|---|---|---|---|
| 8,380,273 | B2 * | 2/2013 | Say et al. | 600/345 |
| 8,409,131 | B2 * | 4/2013 | Say et al. | 604/65 |
| 2003/0191100 | A1 * | 10/2003 | Williams et al. | 514/177 |
| 2003/0219357 | A1 * | 11/2003 | Douglas et al. | 422/58 |
| 2004/0102424 | A1 * | 5/2004 | Williams et al. | 514/172 |
| 2005/0054005 | A1 | 3/2005 | Ellis et al. | |
| 2009/0242399 | A1 * | 10/2009 | Kamath et al. | 204/403.1 |
| 2009/0242425 | A1 * | 10/2009 | Kamath et al. | 205/777.5 |
| 2013/0131469 | A1 * | 5/2013 | Simpson et al. | 600/310 |

FOREIGN PATENT DOCUMENTS

| | | |
|---|---|---|
| EP | 2 130 487 A1 | 12/2009 |
| WO | 2006/111741 A1 | 10/2006 |
| WO | 2008/131224 A2 | 10/2008 |
| WO | 2009/024794 A1 | 2/2009 |

OTHER PUBLICATIONS

Author: Suresh N. Thennadil et al Title: Comparison of Glucose Concentration in Interstitial Fluid, and Capillary and Venous Blood During Rapid Changes in Blood Glucose Levels Date: 2001, Publisher: Mary Ann Lieber, Inc. vol 3, No. 3, 2001.*
Kuwa, et al., Relationships of Glucose Concentrations in Capillary Whole Blood, Venous Whole Blood and Venous Plasma, Clinica Chimica Acta 307, pp. 187-192, 2001.
Kempe, et al., Capillary and Venous Blood Glucose Concentrations Measured During Intravenous Insulin and Glucose Infusion: A Comparison of Steady and Dynamic States, Diabetes Technology & Therapeutics, vol. 11, No. 10, pp. 669-674, 2009.
Eriksson, et al., Capillary-Venous Difference in Blood Glucose Values During the Oral Glucose Tolerance Test, Clinical Chemistry, vol. 29, No. 5, pp. 993-994, 1983.

* cited by examiner

Primary Examiner — Tung S Lau
Assistant Examiner — Stephanie Chang
(74) Attorney, Agent, or Firm — Dinsmore & Shohl LLP

(57) ABSTRACT

Methods for decentralized monitoring of a progression of a diabetic state of a patient include contemporaneously obtaining an initial set of venous blood samples and an initial set of capillary blood samples after a standardized metabolic challenge from the patient in a centralized setting, wherein the diabetic state is diagnosed using the initial set of venous blood samples and a first test baseline is established by correlating the initial set of capillary blood samples with the initial set of venous blood samples, implementing a therapy, performing decentralized testing after reaching a target event, wherein a status test is obtained from a status set of capillary blood samples obtained from the patient after a subsequent standardized metabolic challenge, and comparing the status test with the first test baseline to determine an effectiveness of the therapy.

20 Claims, 4 Drawing Sheets

METHODS AND APPARATUS FOR DECENTRALIZED DIABETES MONITORING

TECHNICAL FIELD

The present disclosure generally relates to monitoring diabetes, and, in particular, to methods and apparatuses for monitoring diabetes in a decentralized environment.

BACKGROUND

The testing and monitoring of diabetes can be accomplished through multiple tests that may independently vary in their accuracy, expense and time demands. While some testing methods may provide a more accurate and acceptable diagnosis, such methods may be relatively time intensive and/or require a laboratory or clinical setting for proper administration. Likewise, other testing methods may be more convenient but provide less accurate or less consistent results impairing their reliability. One test methodology for diagnosing and/or evaluating the diabetic condition of a patient comprises an oral glucose tolerance test (OGTT). An exemplary OGTT can comprise first obtaining a pre-test measurement of the patient's blood glucose after they have fasted for around eight hours. After the pre-test measurement is obtained, a standardized metabolic challenge is administered to the patient to affect the patient's blood glucose level. Test measurements are then obtained on a regimented time table for a defined period of time such that the variations of the patient's blood glucose levels can be monitored. The results of the OGTT can be interpreted by a physician to diagnose or evaluate the diabetic state of the patient.

However, the OGTT can be performed using either venous blood samples or capillary blood samples. Commercial laboratory, or hospital laboratory, methods and equipment using venous blood may provide more accurate and definitive results regarding a patient's diabetic state; however, the testing of venous blood samples is typically performed in a centralized setting such as a clinic. Specifically, a patient must visit a physician's office where their venous blood samples can be drawn over the course of the OGTT. Thereafter, the venous blood samples are shipped for testing at the centralized setting and the results are returned for the physician's review. Capillary blood samples, however, can be far more conducive to testing in a decentralized setting such as at the patient's home using more readily available devices like test strips and portable glucose meters. For example, a portable glucose meter may include a strip port that receives the disposable test strip. The test strip may be coated with chemicals (e.g., glucose oxidase, dehydrogenase, or hexokinase) that combine with glucose in blood allowing it to measure the concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor glucose levels in one's home, or healthcare facility. Patients may thereby perform an OGTT themselves, or when directed by their healthcare professional without, having to visit or ship samples to a third party or endure multiple venipunctures. However, while capillary blood samples allow for more accessible testing, they are often regarded as less reliant and cannot be relied upon in the initial diagnosis of diabetes. Thus, it may be desirable to provide alternative methods and apparatuses for decentralized monitoring of diabetes.

SUMMARY

In one embodiment, a method for decentralized monitoring of a progression of a diabetic state of a patient is provided. The method includes obtaining a pre-test venous blood sample and a pre-test capillary blood sample from the patient after the patient fasts and contemporaneously obtaining an initial set of venous blood samples and an initial set of capillary blood samples from the patient in a centralized setting after a standardized metabolic challenge. The diabetic state is diagnosed using the initial set of venous blood samples and a first test baseline is established by correlating the initial set of capillary blood samples with the initial set of venous blood samples. A therapy is implemented for the patient to address the diabetic state diagnosed by the initial set of venous blood samples. Decentralized testing is performed after reaching a target event. A status test is obtained from a status pre-test capillary blood sample obtained from the patient after the patient fasts and a status set of capillary blood samples obtained from the patient after a subsequent standardized metabolic challenge. The status test is compared with the first test baseline to determine the effectiveness of the therapy.

In another embodiment, an electronic device for decentralized monitoring of a progression of a diabetic state of a patient is provided. The electronic device includes a display and an input terminal for inputting a first test baseline established using an initial set of capillary blood samples. The initial set of capillary blood samples are contemporaneously obtained with an initial set of venous blood samples in a centralized setting. The initial set of venous blood samples being used to diagnose the diabetic state of the patient. The electronic device further includes and a plurality of status tests each established using a status set of capillary blood samples, memory for storing the first test baseline, the plurality of status tests and instructions and a processor in communication with the memory and operable to execute the instructions. The instructions cause the processor to compare the plurality of status tests to the first test baseline such that an effectiveness of a therapy may be determined, the therapy implemented between obtaining the initial set of capillary blood samples and each of the status sets of capillary blood samples.

In yet another embodiment, a decentralized testing kit for decentralized monitoring of a progression of a diabetic state of a patient is provided. The decentralized testing kit includes a plurality of standardized metabolic challenges, a plurality of testing materials operable to obtain an initial set of capillary blood samples and to obtain a status set of capillary blood samples in a decentralized setting after a patient administers one of the plurality of standardized metabolic challenges. The initial set of capillary blood samples are obtained contemporaneously with an initial set of venous blood samples in a centralized setting. The plurality of testing materials are operable to measure a biomarker from each capillary blood sample such that a first test baseline is obtained by correlating the initial set of capillary blood samples with the initial set of venous blood samples and a status test is obtained from the status set of capillary blood samples obtained in the decentralized setting. The decentralized testing kit further includes tracking materials operable to compare the first test baseline with the status test to determine an effectiveness of a therapy implemented between the obtaining of the initial set of capillary blood samples and the status set of capillary blood samples.

These and other advantages and features of the invention disclosed herein, will be made more apparent from the description, drawings and claims that follow.

BRIEF DESCRIPTION OF THE DRAWINGS

The following detailed description of the embodiments of the present disclosure can be best understood when read in conjunction with the following drawings, where like structure is indicated with like reference numerals, and in which.

DETAILED DESCRIPTION

Embodiments of the present disclosure are directed to monitoring diabetes (e.g., progression/regression), and more specifically to monitoring the effectiveness of a prescribed therapy in a decentralized setting. Patients may visit a physician and undergo a first oral glucose tolerance test (OGTT) using venous and capillary blood samples. The first OGTT may be used to diagnose the patient's diabetic state as well as establish a baseline for comparison during subsequent testing and monitoring of the diabetes. The patient, or provider, may then implement some type of therapy to address their diabetic condition until one or more target events are reached. Once a target event is reached, the patient may undergo an additional OGTT in a decentralized setting using capillary blood samples and following the same testing protocols as the first OGTT. The patient may then compare the status test results of the additional decentralized OGTT(s) with the established baseline to see how his or her diabetes is progressing and evaluate the effectiveness of his or her implemented therapy. As a result, patients may possess a more convenient option for monitoring their diabetes through avoiding the time and monetary costs associated with centralized testing.

Figure 1:
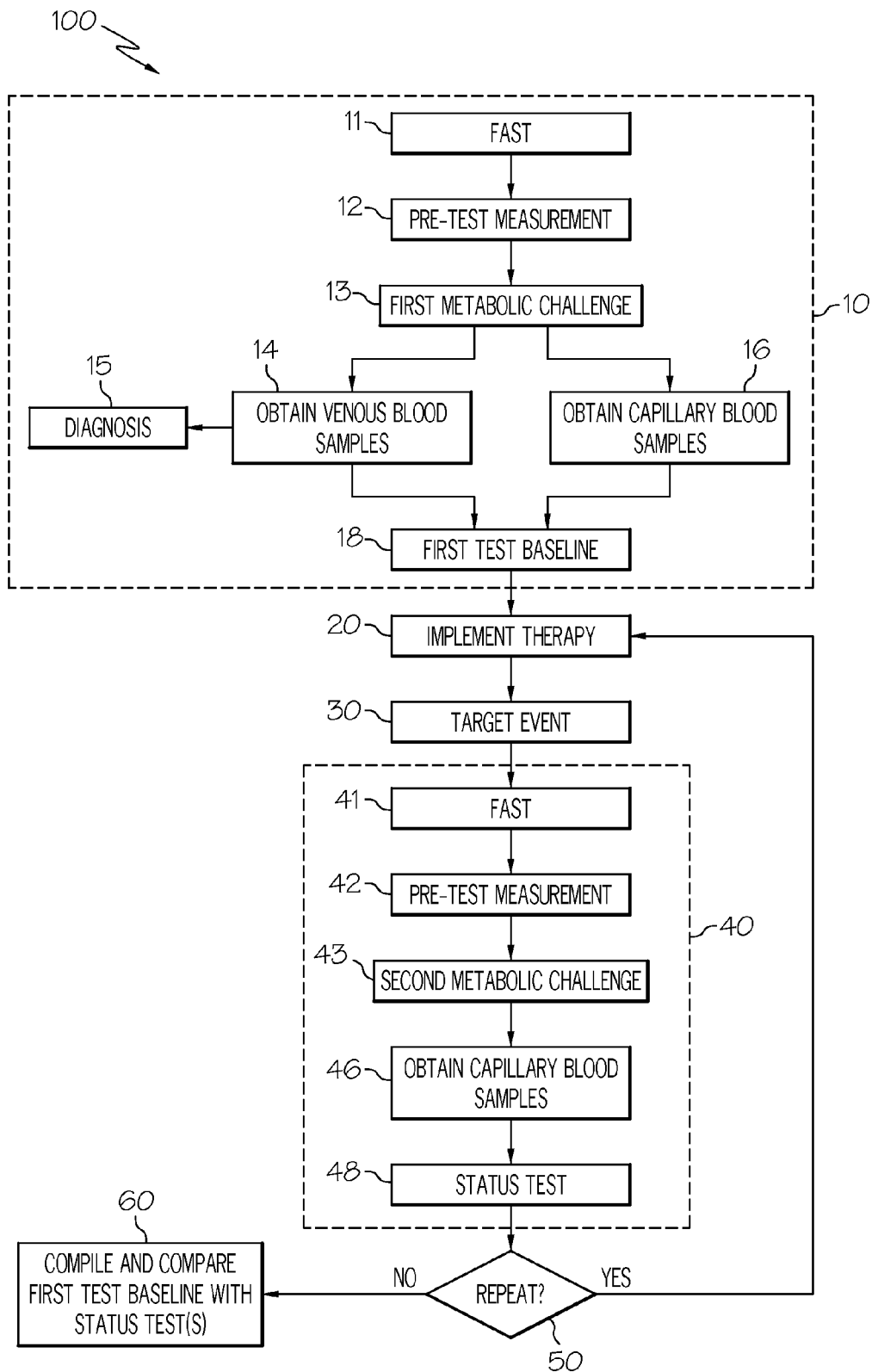
FIG. 1 depicts a logistical flowchart for monitoring diabetes using a decentralized environment according to one or more embodiments shown or described herein.

Referring to FIG. 1, a method 100 for decentralized monitoring of a progression of a diabetic state of a patient is illustrated. The method 100 first comprises initial testing 10 in a centralized setting to diagnose the patient and/or establish a first test baseline as will be discussed herein. As used herein, "centralized setting" refers to a hospital environment (e.g., hospital, physician's office) where both venous and capillary blood samples can be obtained from a patient such as by the patient's physician, nurse or phlebotomist. Specifically, a patient may undergo initial testing 10 to initially evaluate and/or diagnose his or her diabetes. The initial testing can comprise what is generally referred to as an OGTT wherein the patient undergoes a standardized metabolic challenge and the patient's resultant bG response profile is monitored as the patient reacts to the standardized metabolic challenge. Specifically, a patient may first fast in step 11 to allow for a pre-test measurement in step 12. Fasting may occur for any period of time operable to allow for the monitoring of diabetes after undergoing the standardized metabolic challenge. For example, in one embodiment, the patient may fast for about eight hours prior to obtaining the pre-test (i.e., fasting) measurement in step 12. The pre-test measurement may be obtained for any biomarker of the patient. As used herein, "biomarker" refers to any physiological variable that can be measured to provide information relevant to the patient's diabetes. Biomarkers can include, for example, blood glucose (bG), interstitial glucose, heart rate, or blood pressure, which can provide information relevant to the monitoring of diabetes. In one exemplary embodiment, the biomarker comprises the patient's blood glucose such as when obtaining a pre-test venous blood sample and a pre-test capillary blood sample.

Immediately after the pre-test measurement (i.e., the fasting measurement) is obtained from the patient in step 12, the patient is administered a standardized metabolic challenge in step 13. The standardized metabolic challenge administered in step 13 can comprise any standardized substance, or test, given to the patient that incites a change in his or her metabolic system wherein the change can be monitored to gather information relevant to his or her diabetes. For example, in an OGTT, a patient may be given a challenge solution which comprises glucose (such as, for example, anhydrous glucose). In one embodiment, the amount or concentration of the standardized metabolic challenge, such as the amount of glucose in the challenge solution, may depend on the state of the patient such as the type of diabetes the patient may have. For example, in one embodiment, a patient may ingest a 200 milliliter solution containing 75 grams of anhydrous glucose. In another embodiment, such as when the patient has gestational diabetes, the patient may ingest 200 milliliter solution containing 50 grams of anhydrous glucose. It should be appreciated that any other standardized metabolic challenge for testing diabetes may be utilized as long as the same standardized metabolic challenge is utilized throughout the method 100 as will become appreciated herein.

After the standardized metabolic challenge is administered in step 13, blood samples are obtained from the patient to monitor and evaluate the metabolic effect the standardized metabolic challenge had on the patient. Specifically, after the standardized metabolic challenge is administered in step 13, an initial set of venous blood samples may be obtained in step 14 contemporaneously with obtaining an initial set of capillary blood samples in step 16. As used herein, "contemporaneous" and "contemporaneously" means blood samples are taken in substantially the same time period such that the patient's metabolic state is largely the same. In one embodiment, the venous blood samples and capillary blood samples may be obtained simultaneously. In another embodiment, the venous blood samples and capillary blood samples may be obtained in succession, such that one is obtained after the other. In yet another embodiment, a small amount of time (such as a few minutes) may pass between obtaining the venous blood samples and capillary blood samples wherein the patient's metabolic state does not substantially change during the small amount of time. The initial sets of blood samples obtained in step 14 and 16 may be utilized to diagnose the patient's diabetic state in step 15 and/or establish a first baseline test in step 18 as will become appreciated below.

The initial set of venous blood samples obtained in step 14 are obtained from the patient following a diagnosis protocol. As used herein "protocol" refers to the number of blood samples obtained from the patient and the time period between obtaining each sample. For example, in one embodiment, a protocol may comprise five blood samples obtained from the patient at one hour intervals. The venous blood samples obtained in step 14 may then be used to diagnosis the patient's diabetic state in step 15. Diagnosing the patient's diabetic state can comprise analyzing the venous blood samples to evaluate the patient's biomarker information (such as glucose levels) in response to the standardized metabolic challenge to determine whether he or she can be categorized as diabetic. This can further include detailing the disease state classification such as normal glucose tolerance, impaired glucose tolerance (IGT), impaired fasting glucose, or both impaired glucose tolerance and impaired fasting glucose, or any other relevant classification. Specifically, diagnosis in step 15 can occur in a centralized setting wherein the venous blood samples are sent to a laboratory for testing to provide results. Such results may allow for the diagnosis of diabetes according to ADA guidelines by providing accurate and reliable results obtained from the venous blood samples as will become appreciated herein.

In conjunction with diagnosing the patient using venous blood samples, the initial set of capillary blood samples can also be obtained from the patient in step 16. Capillary blood samples may be obtained using any conventional methodology such as lancing devices and hand held glucose meters. The capillary blood samples are obtained following any standardized testing protocol that is capable of being repeated in a decentralized setting (such as at the patient's home). In one embodiment, the testing protocol comprises the same protocol as the diagnosis protocol used in obtaining venous blood samples. In another embodiment, the testing protocol is a simpler protocol such as where the testing protocol may only require obtaining three blood samples while the diagnosis protocol may require obtaining five blood samples. In addition, the testing protocol followed in obtaining the capillary blood samples may be designed to assess certain aspects of the patient's diabetes. For example, in one embodiment, the patient's first and second phase insulin secretion may be analyzed such as to assess the effects of incretin mimetics. In such an embodiment, capillary blood samples may be obtained about every five minutes for up to about 30 minutes. Thus, as will become appreciated later herein, after a patient is given a standardized metabolic challenge, the status test may be obtained by taking capillary blood samples at about 5, 10, 15, 20, 25 and 30 minutes after the standardized metabolic challenge to evaluate the first and second phase secretion. In other embodiments, the health care provider may create a testing protocol specific for the patient that considers the time to peak metabolic activity based on the implemented therapy, standardized metabolic challenge and/or other testing parameters as will become appreciated herein.

The biomarker values are thereby measured from the initial set of capillary blood samples and set as the first test baseline in step 18. The first test baseline can comprise the patient's biomarker values that are a reaction to the standardized metabolic challenge and obtained according to the testing protocol. Specifically, while the venous blood samples allow for an accurate diagnosis of the patient's diabetes using centralized evaluation, the capillary blood samples provide a decentralized baseline of the patient's metabolic status. The capillary blood samples may thereby be correlated with the venous blood samples such that improvement shown in subsequent capillary blood samples may be interpreted as improvements in light of venous blood samples. For example, in one embodiment, the initial set of venous blood samples (obtained in step 14) and the initial set of capillary blood samples (obtained in step 16) may be mathematically correlated in establishing the first test baseline in step 18 such that future capillary blood samples (e.g., capillary blood samples obtained in step 46 as will become appreciated herein) can be transposed by the mathematical correlation to establish a status test that can relate to the venous blood samples. The mathematical correlation between the initial set of venous blood samples and initial set of capillary blood samples can comprise any correlation operable to allow future capillary blood samples to be compared to the initial venous blood samples. For example, a mathematical equation can be used to translate the initial set of capillary blood samples into the initial set of venous blood samples and vice-versa. Such a mathematical equation can then be used to translate future sets of capillary blood samples into theoretical sets of venous blood samples for diagnostic comparison. Any operable known mathematical correlation method can be used depending on the type and amount of data obtained. In one embodiment, the mathematical correlation between the initial set of venous blood samples and initial set of capillary blood samples may be specific to the patient from whom the samples were obtained. In another embodiment, a subsequent set of venous blood samples and a subsequent set of capillary blood samples may also be mathematically correlated to verify the original correlation still holds substantially true to translating the capillary blood samples to venous blood samples. By obtaining both sets of information (i.e., venous blood samples and capillary blood samples) using standardized and repeatable testing protocols, the patient's diabetes may be accurately diagnosed in accordance with ADA guidelines while further allowing for the decentralized monitoring of both the progress and the effectiveness of prescribed therapies.

Once the first test baseline is established in step 18, a therapy is implemented in step 20. The therapy implemented in step 20 may comprise any drug, activity, routine change or other habitual undertaking that can affect the patient's diabetes. The therapy may be determined by the physician, the patient or a combination of the two. In one embodiment, the therapy may depend on the type, classification or severity of the diabetes as determined from the diagnosis in step 15 using the venous blood samples obtained in step 14. Specifically, a patient may progress through a series of different tiers of therapies intended to address different diabetic states or different physiological pathways relevant to the patient's diabetic state. For example, a patient may first implement a "tier 1" therapy substantially comprising improved diet and exercise or taking metformin. The tier 1 therapy may be designed for patients who are only borderline diabetic such as by targeting improving fasting plasma glucose. Depending on the state of the patient and/or the effect of the tier 1 therapy, the patient may alternatively or additionally implement a "tier 2" therapy substantially designed to increase insulin production in the patient such as by taking a sulfonylurea. If necessary, the patient may then advance to a more significant "tier 3" therapy comprising, for example, taking incretin memetics. Finally, the patient may advance to a "tier 4" therapy comprising insulin injections. In another embodiment, the therapy may be determined using a combination of evaluations such as impaired fasting and impaired glucose tolerance. It should be appreciated that any therapy may be implemented in step 20 that can influence the patient's disease state and allow for the monitoring of the effectiveness of the therapy on the patient.

The therapy is thereby implemented in step 20 until a target event is reached in step 30. The target event can comprise any point in time or any type of milestone reached since the beginning of the therapy implementation. In one embodiment, the target event may depend on the type of therapy implemented. For example, where the therapy implemented in step 20 comprises a lifestyle change (such as eating smaller portions or engaging in more physical activity), the target event can comprise the duration of a period of time such as a certain amount of weeks. In another embodiment, the target event may be inherent in the therapy such as comprising the completion of the therapy. For example, where the therapy implemented in step 20 comprises a prescribed drug, the target event can comprise the completion of one regiment of the drug. In yet another example, the target event may simply comprise the next physician's appointment or other arbitrary date established by the patient and/or physician. It should be appreciated that the target event in step 30 can thereby comprise any type of amount, time or any other type of measurable data.

After the occurrence of the target event in step 30, the patient undergoes decentralized testing 40 to evaluate the status of his or her diabetes with respect to his or her first test baseline (as obtained in step 18). As used herein, "decentralized testing" and "decentralized environment" refer to testing capillary blood samples outside of the hospital environment (e.g., hospital, physician's office) in which the centralized testing occurred. For example, as the decentralized testing does not require a centralized laboratory for the evaluation of results, decentralized testing 40 can occur at the patient's home, work or any other place outside of the centralized hospital. To obtain the status of his or her diabetes, the patient undergoes the same standardized testing protocol utilized in step 11 during the initial testing 10. Thus, the patient fasts in step 41 in a similar manner as occurred in step 11 during the initial testing 10. After fasting is completed in step 41, a pre-test measurement is obtained in step 42. The pre-test measurement measures the same type of biomarker information that was recorded in the initial testing 10. For example, where the biomarker obtained in initial testing 10 comprised blood glucose, such as by obtaining a pre-test venous blood sample and a pre-test capillary blood sample, the pre-test measurement obtained in step 42 (and subsequent measurements on capillary blood samples) would also comprise blood glucose, such as by obtaining a status pre-test capillary blood sample. After the pre-test measurement is obtained in step 42 of the decentralized testing 40, a subsequent standardized metabolic challenge is administered in step 43. The subsequent metabolic challenge (i.e., the second metabolic challenge) administered in step 43 comprises a metabolic challenge that is the same or substantially similar to the standardized metabolic challenge administered in step 13 during the initial testing 10 such that a standardized test is administered and consistent conditions apply towards evaluating the status of the patient's diabetes. Finally, after the subsequent standardized metabolic challenge is administered in step 43, a status set of capillary blood samples are obtained in step 46. The status set of capillary blood samples obtained in step 46 can be obtained using the same testing protocol, such as being obtained at the same standardized time intervals (e.g., at about 5, 10, 15, 20, 25 and 30 minutes after administering the standardized metabolic challenge) such that consistent measurements are taking post the standardized metabolic challenge compared to the initial testing. Such standardized testing may allow for reputable evaluations of one or more therapies by ensuring consistent conditions between both centralized and decentralized testing. For example, where the testing protocol used to obtain capillary blood samples in step 16 of initial testing 10 comprised obtaining five samples at one-hour intervals, the patient may similarly obtain five capillary blood samples also at one-hour intervals in step 46 during the decentralized testing 40. The capillary blood samples may be obtained in step 46 through any a conventional methodology such as lancing devices and hand held glucose meters. In one embodiment, the same methodology used to obtain capillary blood samples in step 16 during initial testing may be used to obtain capillary blood samples 46 during decentralized testing 40. In another embodiment, the same piece of equipment (such as a patient owned glucose meter) may be used to obtain both the initial set of capillary blood samples and the status set(s) of capillary blood samples. In yet another embodiment, a comparable pieces of equipment (such as the same model, or devices that gives substantially the same results) may be used to obtain the initial set of capillary blood samples and the status set(s) of capillary blood samples.

After the status set of capillary blood samples is obtained in step 46 of the decentralized testing, the status test is determined by evaluating the biomarker values for each capillary blood samples. The status test comprises a plurality of biomarker values based on the capillary blood samples. For example, where five capillary blood samples were obtained in step 46, the status test can comprise five blood glucose levels as measured from each of the individual capillary blood samples. The status test determined in step 48 of the decentralized testing 40 may then be compared to the first test baseline determined from step 18 of initial testing 10 to evaluate the change in the patient's diabetes status and determine the effectiveness (or lack thereof) of the therapy implemented in step 20. Specifically, the status test obtained in step 48 may be compared to the first test baseline obtained in step 18 to evaluate the changes the patient has undergone with respect to his or her diabetes. Where the therapy implemented in step 20 was effective, the patient should see an improved reaction to the standardized metabolic challenge. Conversely, where the therapy was ineffective, or his or her diabetes progressed, the patient would see a less promising reaction to the standardized metabolic challenge.

After the status test is obtained in step 48, the process may be repeated at step 50 to either allow for further evaluation of a given therapy or allow for the evaluation of a different therapy for the comparison of their effectiveness. For example, where the status test obtained in step 48 illustrates improvement in the health of the patient when compared to the first test baseline 18, the same type of therapy may be continued to be implemented in step 20 and a new target event may be established for step 30. However, if the status test obtained in step 48 shows progression of the patient's diabetes, or not as much improvement as expected, the patent and/or his or her physician may decide to implement a subsequent therapy in step 20 and subsequent target event in step 30 for an alternative approach to addressing his or her health. It should be appreciated that the implementation of therapy in step 20 and the corresponding decentralized testing 40 used to evaluate the effectiveness of that therapy may be repeated for as many or as few times as the patient and/or his or her physician wishes to allow for the monitoring of a diabetic condition. In one embodiment, two or more drugs may be compared (such as a generic drug and a non-generic drug) to evaluate the relative effectiveness of each. In such an example, the patient may undergo one month using the generic drug followed by a round of decentralized testing 40. The patient may then switch to the non-generic drug for the next month and conclude with yet another round of decentralized testing 40. The comparisons of status tests for each month (either compared to the first test baseline or to one another) may thereby allow for the determination of the relative effectiveness of each drug.

In another particular embodiment, a subsequent therapy may be implemented subsequent to the first therapy such that the effect each therapy has on the patient may be individually determined and compared. For example, after decentralized testing 40 is completed for a first therapy, a second therapy may be implemented. Then, decentralized testing may be performed wherein a second status test is obtained from a second status set of capillary blood samples after the patient takes an additional standardized metabolic challenge the same as or substantially similar to the previous standardized metabolic challenges. In obtaining the second set of capillary blood samples, the same testing protocols may be followed as used in obtaining the initial set of capillary blood samples (used for establishing the first test baseline) and the other set of capillary blood samples (used for the status test of the first implemented therapy). The second status test may then be compared to the first test baseline to determine the effectiveness of the second therapy. Finally, the effectiveness of the first therapy may be compared to the effectiveness of the second therapy. Such comparisons may provide valuable insight as to which therapies are most beneficial to a particular patient or situation. For example, where the first therapy comprises a first anti-diabetic drug, the second therapy may comprise a different anti-diabetic drug or the generic version of the first anti-diabetic drug such that the relative impact of each drug may be evaluated. In one embodiment, the patient may undergo a washout period between obtaining the status test from the status set of capillary blood samples and implementing the second therapy. The washout period may comprise any period of time wherein the patient does not implement either therapy so that the first therapy is effectively washed out of the patient prior to implementing the second therapy. For example, where the first therapy comprises taking an anti-diabetic drug for one month, the patient may undergo a washout period of one or more weeks to ensure the first anti-diabetic drug is substantially removed from the patient. The patient may then either obtain new capillary blood samples to effectively determine the patient's disease status post the first therapy, or may then implement a second therapy as described above. Using such comparisons, the cost-benefit of particular drugs or the overall success rate of particular drugs may be evaluated.

Figure 2:
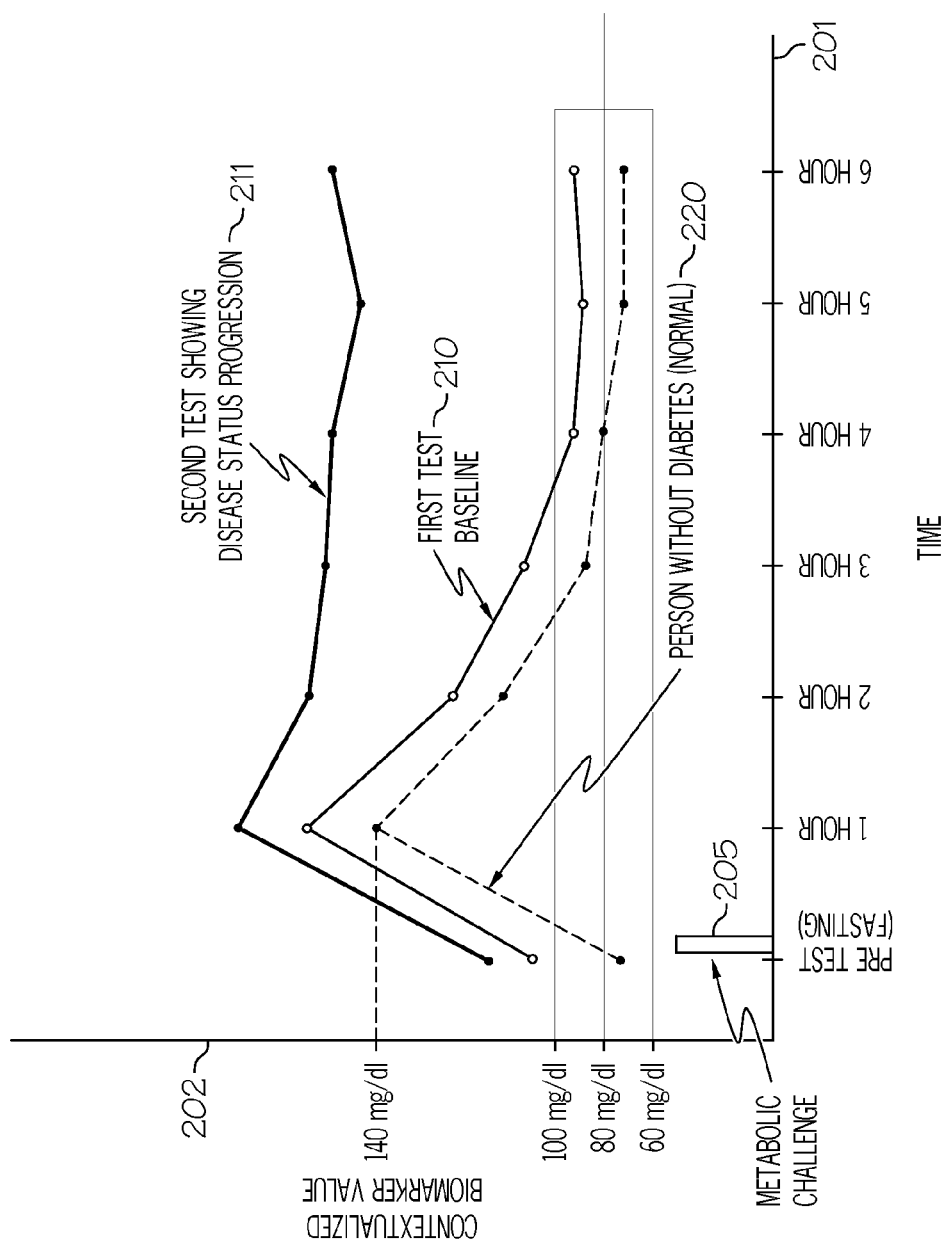
FIG. 2 depicts an exemplary chart for comparing a first test baseline with a status test and a reference test according to one or more embodiments shown or described herein.

If the implementation of therapy in step 20 and decentralized testing 40 is not to be repeated in step 50, the results of the first test baseline obtained in step 18 may be compared with the results of each status test in step 48. Compiling and comparing the results of the first test baseline and the one or more status tests can comprise any method to evaluate the changes between the two states. For example, referring to FIG. 2, a chart is illustrated comprising a patient's first test baseline 210 (as obtained in step 18 of the method 100 for decentralized monitoring of a progression of a diabetic state of a patient illustrated in FIG. 1) and a comparative second test 211 (as obtained in step 48 of the method 100 for decentralized monitoring of a progression of a diabetic state of a patient illustrated in FIG. 1). The chart plots the biomarker values 202 (in this example, the biomarker values comprise bG values) measured from the capillary blood samples as dependent on the time period 201. Specifically, the standardized metabolic challenge 205 is administered shortly after the pre-test measurement is obtained. Then, bG values are obtained every hour for six hours to monitor the patient's bG values as his or her metabolic system reacts to the standardized metabolic challenge. The first test baseline 210 represents the patient's reaction as determined from when he or she was diagnosed during initial testing. A status test 211 overlaid on the same chart allows for the comparison of the patient's reaction after a certain target event to see the effectiveness (or lack thereof) of the implemented therapy. For reference, a typical reaction 220 from a non-diabetic patient may also overlaid to allow for the visualization of the patient's overall diabetic state.

By obtaining capillary blood samples and obtaining biomarker values in a decentralized environment, the patient may conveniently monitor the status of his or her diabetes without the inclusion of centralized evaluation. The patient may thereby only incur the temporal and monetary inconvenience of using a centralized testing center when first diagnosing his or her diabetic state using venous blood samples. The simultaneous obtainment of capillary blood samples allows for an accurate first test baseline that can be correlated with his or her initial diabetic diagnosis and allow for the future evaluation of his or her disease and the effectiveness of therapy.

Figure 3:
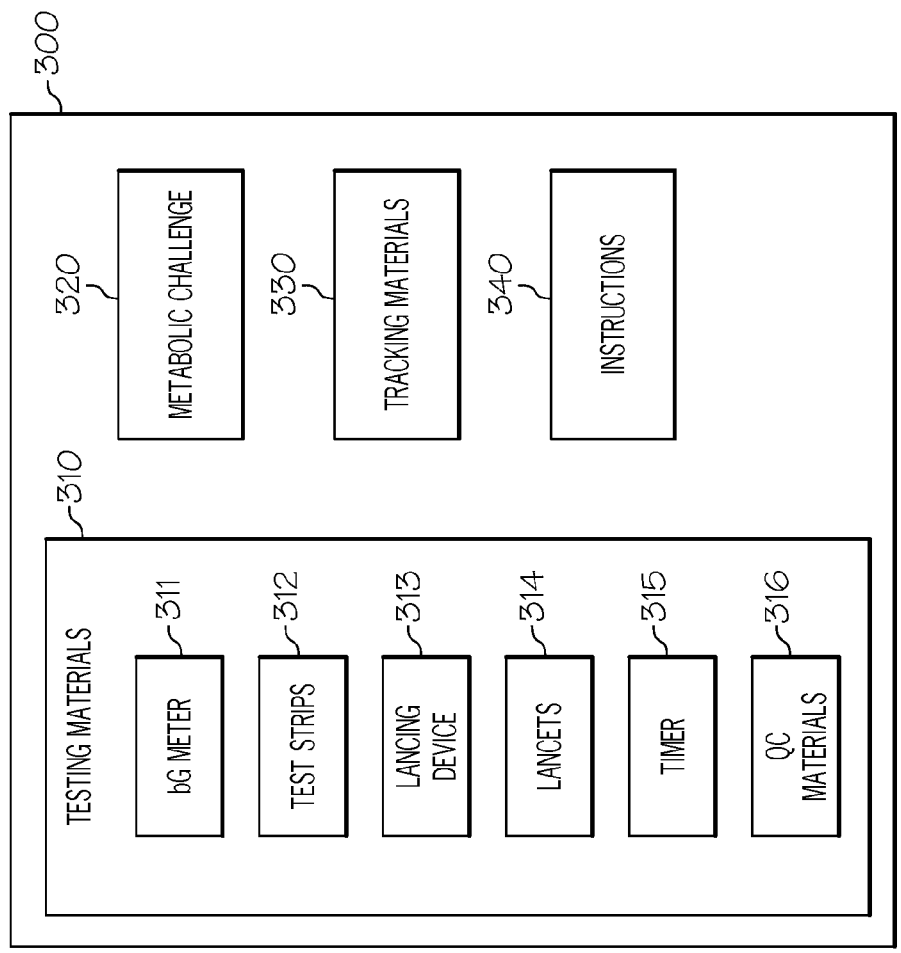
FIG. 3 depicts an exemplary decentralized testing kit according to one or more embodiments shown or described herein, and, FIG. 4 depicts an exemplary electronic device for the decentralized monitoring of diabetes according to one or more embodiments shown or described herein.

Referring now to FIG. 3, a decentralized testing kit 300 may be provided to facilitate the decentralized monitoring of a progression of a diabetic state of a patient. The decentralized testing kit 300 may comprise any and all components necessary for a patient to monitor his or her diabetes and the effectiveness of implemented therapy using decentralized testing. For example, in one embodiment, the decentralized testing kit 300 may first comprise testing materials 310. Testing materials 310 can comprise a bG meter 311, test strips 312, lancing devices 313, lancets 314 and/or a timer 315 to facilitate the obtaining of capillary blood samples and measure the appropriate biomarker values following a specified testing protocol. In one embodiment, the timer 315 may be integral with the bG meter 311 such that the bG meter itself reminds or instructs the patient when to obtain the various capillary blood samples in accordance with the standardized testing protocols. In another embodiment, the decentralized testing kit 300 may further comprise other quality control materials 316 to assist the patient in following the standardized testing protocol such as, for example, visual aids, example materials or other reminder-oriented tools. The decentralized testing kit 300 may further comprise one or more standardized metabolic challenges 320 as administered in steps 13 and 43 of the method 100 for decentralized monitoring of a progression of a diabetic state of a patient illustrated in FIG. 1. Tracking materials 330 may further be provided in the decentralized testing kit 300 to allow for the compiling and comparison of the first test baseline with one or more status tests. The tracking materials can comprise any graph, chart or electronic medium to enter and display the results such that the patient and/or physician may compare status tests with the first test baseline. Finally, the decentralized testing kit 300 may further comprise instructions 340 for the patient on how to obtain blood samples, how to obtain biomarker values, how to compare results and/or any other procedural guidelines potentially useful for the patient.

Figure 4:
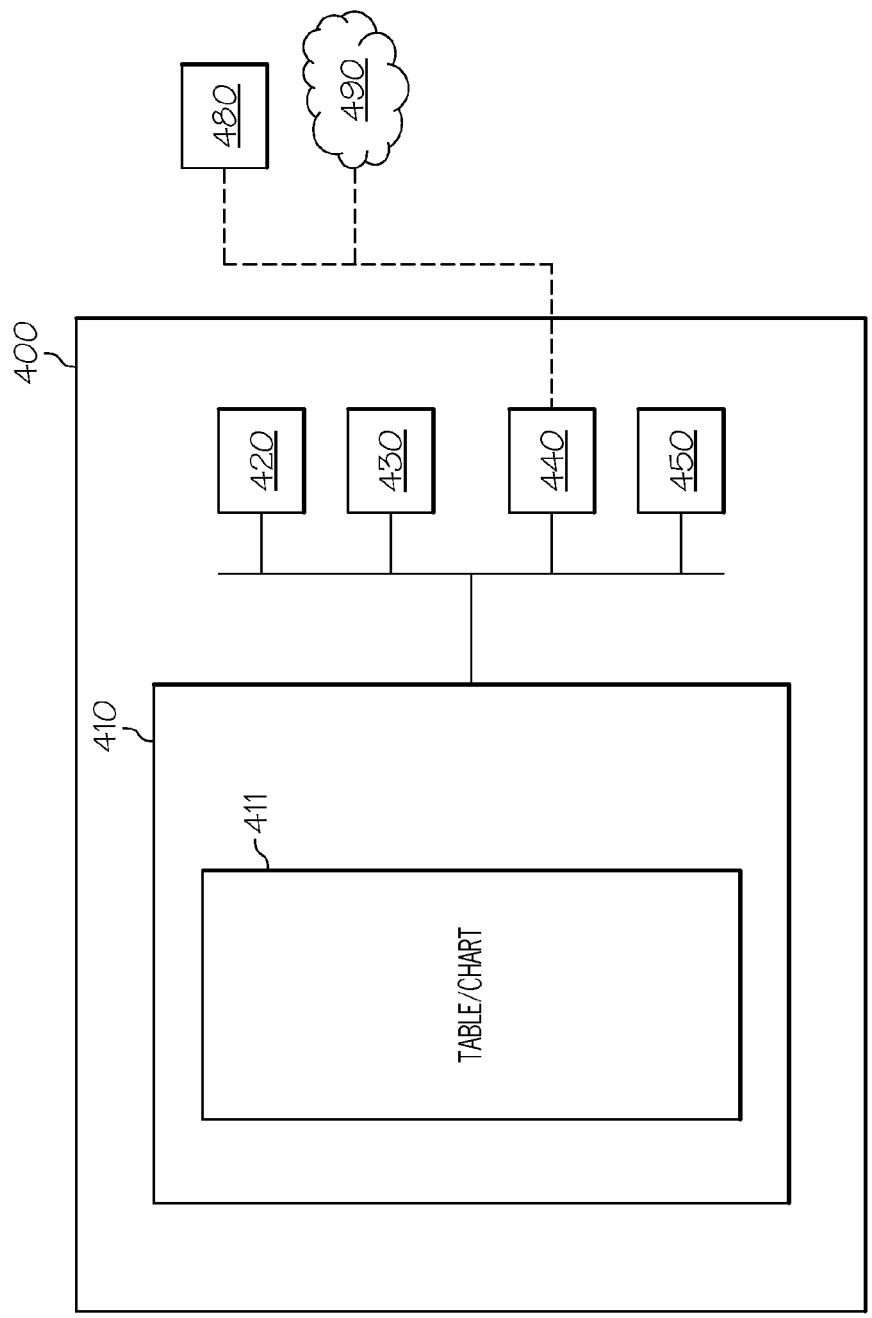

Referring now to FIG. 4, in another embodiment, an electronic device 400 may be provided to obtain, store, compile and/or display a first test baseline and one or more status tests. For example, in one embodiment, the electronic device 400 may comprise a display 410 for showing a table or chart 411 comparing one or more status tests with the first test baseline. The electronic device 400 may further comprise a processor 420, memory 430, and one or more input terminals 440, 450. The processor 420 may process information such as computing changes between biomarker values or evaluating differences between a first test baseline and one or more status tests. The memory 430 may be operable to store the programs mentioned earlier and in sections hereafter, program instructions which cause the processor 420 to perform the steps of method 100, and information such as measurements, target events, testing protocols or operator preferences. The input terminal 450 may comprise any mechanism for inputting data, operator feedback or other information for routine handling by the processor of the device. For example, in one embodiment the electronic device 400 may comprise an input terminal for receiving biomarker values (as measured from capillary blood samples) and another input terminal (such as a keyboard or a touch screen) for operator communication of timing and protocols. In addition, examples of routine handling may include the processor 420 storing input received via the input terminal 450 into the memory 430, or retrieving information from the memory 430 based on input received via the input terminal 450, like a request to display the compiled results of a completed comparison.

For example, a patient may enter the date and time of his or her initial testing (illustrated as step 10 in FIG. 1) into the electronic device 400 via the input terminal 450. The biomarker values used to determine the first test baseline may then be obtained manually by the user or automatically by the electronic device 400. For example, in one embodiment, the user may manually test his or her blood (step 16 in FIG. 1), such as with test strips and/or a separate glucose meter, and enter the resulting biomarker measurements into the electronic device 400 via the input terminal 450. In yet another embodiment, such as where the electronic device 400 comprises a blood glucose meter, the electronic device may itself obtain the capillary blood samples and automatically measure the biomarker values and record them to the memory 430 to determine the first test baseline (steps 16 and 18 in FIG. 1). The user of the electronic device 400 may then implement his or her therapy and wait for the target event to occur (steps 20 and 30 in FIG. 1). In one embodiment, such as when the therapy is to be implemented for a certain number of days, the target event may be entered into the electronic device via input terminal 450 and record in memory 430 such that the electronic device 400 can remind the patient when the target event occurs.

The patient may then use the electronic device 400 for decentralized testing (step 40 in FIG. 1) or the storing and compiling of data obtained from decentralized testing. For example the electronic device can collect and compile the biomarker values comprising one or more status tests (step 48 in FIG. 1) and compare such results to the first baseline test on the chart 411 of the display 410.

In another embodiment, the electronic device 400 may be part of an information system, such as, for example, where a server 480 provides instructions and stores information such as the first test baseline, the status tests and/or the types of therapy or target events. In such an embodiment, the server 480 may communicate either directly or over a network 490, e.g., LAN, WAN, Internet, and the like, with the electronic device 400 via communications hardware 440 enabling wired and/or wireless communications therewith. In this manner, the complied results from any status test may be downloaded or sent to a healthcare provider and/or another software tool for adding notes and/or to allow further evaluations and recommendations. For example, in one embodiment, the software tool may send back over the network 490 to the electronic device 400 new therapy suggestions such as coaching tips for meals and exercises changes that are based on the comparisons of status tests. As the communication hardware 440, server 480, and network 490 are conventional and well understood by those skilled in the art, no further discussion is provided.

In one particular embodiment, the processor 420 is in communication with the memory 430 (and/or server 480) and operable to execute instructions stored therein. The instructions when executed by the processor 420 cause the processor to compile the obtained biomarker values to establish the first test baseline and the one or more status tests as well as compile and compare the results of such.

In other embodiments, the electronic device 400 may be, but not be limited to, a blood glucose meter, a personal digital assistant (PDAs), a cell phone, a smart phone, an electronic logbook or any other computing device such as a laptop, a desktop or web-based computing platform. In still another embodiment, the display 410 may be accessed through a program capable of being installed on or accessed by various computers, hand held devices or the like. Furthermore, the display 410 may comprise a full color screen, a black and white screen, a monochromatic screen or any other color variation. The display 410 may comprise a liquid crystal display (LCD), a plasma display, a cathode ray tube (CRT), a projection display or any alternative technology operable to display comparisons of status tests with a first test baseline for a patient and/or their physician.

To help illustrate the above benefits provided by the embodiments of the present invention, the following use case example is provided. In this use case example, a physician, suspicious of diabetes, performs a random bG measurement on a patient and discovers the measurement to be highly elevated. The health care provider therefore schedules a second visit for a formal diagnostic and the patient revisits at a later date. As instructed by the physician, prior to the follow-up visit, the patient fasts for the requisite amount of time to obtain a pre-test measurement. Once at the physician's office, the physician obtains a pre-test measurement of the patient's current bG. At the same time, the patient is also provided with a decentralized testing kit that includes a blood glucose meter and multiple standardized metabolic challenges. The patient then ingests one of the standardized metabolic challenges as instructed by the physician. After administering the standardized metabolic challenge, a series of venous blood samples are obtained every hour for five hours. Contemporaneously, the patient utilizes the glucose meter to obtain and test capillary blood samples for his or her blood glucose level. The venous blood samples are sent to an outside lab for testing and evaluation and it is determined that the patient has diabetes. The blood glucose levels obtained by the patient using the glucose meter are thereby established as the first test baseline for the monitoring of his or her diabetic state.

As a result of the diabetic diagnosis, the physician prescribes a therapy, such as a sulfonylurea, which the patient takes for one month. After one month, the patient uses the decentralized testing kit (and specifically the glucose meter) to perform decentralized testing and obtain a first status test. Specifically, the patient fasts, obtains a pre-test measurement, administers the standardized metabolic challenge, and obtains and measures capillary blood samples every hour for five hours after ingesting the standardized metabolic challenge. The glucose meter compiles the blood glucose levels for the newly obtained capillary blood samples and establishes a first status test that is compared to the first test baseline. As a result of the comparison, it is appreciated that the patient's diabetes is not progressing. The physician may then instruct the patient on improved eating habits and/or encourage an increased amount of physical activity over the next month. The patient may then undergo a new round of decentralized testing to establish a second status test to see if his or her diabetes is improving as a result of the newly prescribed lifestyle changes.

It should now be appreciated that decentralized testing may be utilized to monitor a patient's diabetes and evaluate the effectiveness of one or more implemented therapies. The embodiments of the present invention can help a patient and physician know, for example, whether prescribed thereby is effective in addressing the patient's diabetes without requiring the time and monetary intensive process or repetitious centralized testing. By correlating the initial diagnosis with a first test baseline, future status tests may effectively be compared to the first test baseline to gauge the patient's diabetic state and know whether an implemented therapy is working.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A method for decentralized monitoring of a progression of a diabetic state of a patient with use of an electronic device, the method comprising: obtaining a pre-test venous blood sample and a pre-test capillary blood sample from the patient after the patient fasts obtaining an initial set of venous blood samples and an initial set of capillary blood samples from the patient in a centralized setting after a standardized metabolic challenge, wherein the diabetic state is diagnosed using the initial set of venous blood samples and wherein a first test baseline is established by correlating the initial set of capillary blood samples with the initial set of venous blood samples; implementing a therapy for the patient to address the diabetic state diagnosed by the initial set of venous blood samples; performing decentralized testing after reaching a target event, wherein a status test is obtained from a status pre-test capillary blood sample obtained from the patient after the patient fasts and from a status set of capillary blood samples obtained from the patient after a subsequent standardized metabolic challenge; and comparing the status test with the first test baseline to determine an effectiveness of the therapy.

2. The method of claim 1, wherein performing decentralized testing is repeated such that a plurality of status tests are compared with the first test baseline.

3. The method of claim 1 further comprising prescribing a subsequent therapy for the patient based on the effectiveness of the therapy.

4. The method of claim 3, wherein the subsequent therapy is a repeat of the therapy.

5. The method of claim 3 wherein the subsequent therapy is implemented based on comparing the status test with the first test baseline.

6. The method of claim 1, wherein the first test baseline and the status test comprises a plurality of biomarker values.

7. The method of claim 6, wherein the plurality of biomarker values comprise measurements of a patient's glucose level, interstitial glucose level, heart rate or blood pressure.

8. The method of claim 1, wherein the initial set of capillary blood samples and the status set of capillary blood samples are obtained at standardized time intervals.

9. The method of claim 1, wherein the target event comprises a duration of time since the implementing the therapy.

10. The method of claim 1, wherein the therapy depends on the diabetic state.

11. The method of claim 1, further comprising:
implementing a subsequent therapy;
performing decentralized testing after reaching a subsequent target event, wherein a second status test is obtained from a second status set of capillary blood samples obtained from the patient after an additional standardized metabolic challenge;
comparing the second status test with the first test baseline to determine an effectiveness of the subsequent therapy; and
comparing the effectiveness of the therapy to the effectiveness of the subsequent therapy.

12. The method of claim 11, wherein a washout period is undergone between obtaining the status test from the status set of capillary blood samples and implementing the subsequent therapy.

13. An electronic device for decentralized monitoring of a progression of a diabetic state of a patient, the electronic device comprising:
a display;
an input terminal for inputting a first test baseline established using an initial set of capillary blood samples, wherein the initial set of capillary blood samples were obtained with an initial set of venous blood samples in a centralized setting, the initial set of venous blood samples being used to diagnose the diabetic state of the patient, and a plurality of status tests each established using a status set of capillary blood samples;
memory for storing the first test baseline, the plurality of status tests and instructions; and
a processor in communication with the memory and operable to execute the instructions, the instructions causing the processor to compare the plurality of status tests to the first test baseline such that an effectiveness of a therapy may be determined wherein the therapy was implemented between obtaining the initial set of capillary blood samples and each of the status sets of capillary blood samples.

14. The electronic device of claim 13, wherein the electronic device comprises a blood glucose meter.

15. The electronic device of claim 14, wherein the first test baseline and the plurality of status tests are each obtained using the blood glucose meter.

16. The electronic device of claim 13, wherein the first test baseline and each of the plurality of status tests comprise a plurality of biomarker values.

17. The electronic device of claim 16, wherein the plurality of biomarker values comprise measurements of a patient's glucose level, interstitial glucose level, heart rate or blood pressure.

18. A decentralized testing kit for decentralized monitoring of a progression of a diabetic state of a patient, the decentralized testing kit comprising:
a plurality of standardized metabolic challenges;
a plurality of testing materials operable to obtain an initial set of capillary blood samples and to obtain a status set of capillary blood samples in a decentralized setting after a patient administers one of the plurality of standardized metabolic challenges, wherein the initial set of capillary blood samples are obtained with an initial set of venous blood samples in a centralized setting and wherein the plurality of testing materials are operable to measure a biomarker from each capillary blood sample such that a first test baseline is obtained by correlating the initial set of capillary blood samples with the initial set of venous blood samples and a status test is obtained from the status set of capillary blood samples obtained in the decentralized setting; and
tracking materials operable to compare the first test baseline with the status test to determine an effectiveness of a therapy implemented between the obtaining of the initial set of capillary blood samples and the status set of capillary blood samples.

19. The decentralized testing kit of claim 18 further comprising a glucose meter or a plurality of test strips.

20. The decentralized testing kit of claim 18 further comprising a lancing device and a plurality of lancets.

* * * * *